United States Patent
Dave et al.

(10) Patent No.: US 8,945,598 B2
(45) Date of Patent: *Feb. 3, 2015

(54) LOW TEMPERATURE DRYING METHODS FOR FORMING DRUG-CONTAINING POLYMERIC COMPOSITIONS

(75) Inventors: Vipul Dave, Hillsborough, NJ (US); Murty N. Vyakamam, South Orange, NJ (US); Qiang Zhang, Annandale, NJ (US)

(73) Assignee: Cordis Corporation

( * ) Notice: Subject to any disclaimer, the term of this patent is extended or adjusted under 35 U.S.C. 154(b) by 1681 days.

This patent is subject to a terminal disclaimer.

(21) Appl. No.: 11/321,014

(22) Filed: Dec. 29, 2005

(65) Prior Publication Data

US 2007/0154512 A1   Jul. 5, 2007

(51) Int. Cl.
| A61L 33/00 | (2006.01) |
| A61K 9/70 | (2006.01) |
| A61K 9/00 | (2006.01) |
| A61L 31/10 | (2006.01) |
| A61L 31/16 | (2006.01) |

(52) U.S. Cl.
CPC ............. *A61K 9/7007* (2013.01); *A61K 9/0024* (2013.01); *A61L 31/10* (2013.01); *A61L 31/16* (2013.01); *A61L 2300/62* (2013.01)
USPC ........... 424/423; 424/422; 424/486; 528/480; 528/502 R

(58) Field of Classification Search
None
See application file for complete search history.

(56) References Cited

U.S. PATENT DOCUMENTS

| 5,330,783 | A | * | 7/1994 | Saidman et al. ................... 427/8 |
| 5,456,917 | A | * | 10/1995 | Wise et al. ..................... 424/426 |
| 6,702,850 | B1 | * | 3/2004 | Byun et al. .................. 623/1.44 |
| 7,294,406 | B2 | * | 11/2007 | Canham et al. ................. 428/446 |
| 8,273,404 | B2 | * | 9/2012 | Dave et al. .................... 427/2.24 |
| 2003/0008238 | A1 | * | 1/2003 | Goldfarb et al. ............ 430/272.1 |
| 2003/0125513 | A1 | * | 7/2003 | King ............................... 528/480 |
| 2004/0018240 | A1 | * | 1/2004 | Ohmachi et al. ............... 424/486 |
| 2004/0109952 | A1 | * | 6/2004 | Jagannathan et al. ........ 427/458 |
| 2004/0126405 | A1 | * | 7/2004 | Sahatjian et al. ............. 424/423 |
| 2004/0199241 | A1 | * | 10/2004 | Gravett et al. ............... 623/1.13 |
| 2005/0037086 | A1 | * | 2/2005 | Tyo et al. ...................... 424/489 |
| 2005/0240254 | A1 | * | 10/2005 | Austin .......................... 623/1.11 |
| 2006/0047336 | A1 | * | 3/2006 | Gale et al. ..................... 623/1.11 |

FOREIGN PATENT DOCUMENTS

| EP | 0 562 864 A | 9/1993 |
| EP | 0 838 491 A | 4/1998 |
| EP | 1683560 A1 | 7/2006 |
| GB | 2 301 362 A | 12/1996 |
| WO | WO 93/24150 A | 12/1993 |
| WO | WO2004062560 A2 | 7/2004 |
| WO | WO2004096173 A2 | 11/2004 |
| WO | PCT2005531408 A | 10/2005 |

OTHER PUBLICATIONS

Witschi, Claudia; and Doelker, Eric; "Residual solvents in pharmaceutical products: acceptable limits influences on physicochemical properties, analytical methods and documented values," 1997, Elsevier; European Journal of Pharmaceutics and Biopharmaceutics, vol. 43, pp. 215-242.*

* cited by examiner

*Primary Examiner* — David J Blanchard
*Assistant Examiner* — Ivan Greene

(57) ABSTRACT

The present invention relates to a process for reducing solvent contents in drug-containing polymeric compositions. Specifically, the solvent contents in the drug-containing polymeric compositions are first reduced by one or more conventional drying methods, to a range from about 0.5 wt % to about 10 wt % of the total weight of the polymeric composition. Subsequently, the drug-containing polymeric compositions are further treated by one or more low temperature (i.e., having processing temperatures of less than 60° C.) drying methods for further reduction of the solvent content to less than 10,000 ppm.

1 Claim, No Drawings

LOW TEMPERATURE DRYING METHODS FOR FORMING DRUG-CONTAINING POLYMERIC COMPOSITIONS

FIELD OF THE INVENTION

The present invention relates to methods for removing solvent(s) from drug-containing polymeric compositions that form implantable medical devices (or at least portions thereof) or form coatings over implantable medical devices (or at least over portions thereof).

BACKGROUND OF THE INVENTION

In recent years, drug-eluting implantable medical devices, such as, for example, stents, stent grafts, anastomosis devices, vascular grafts, vascular patches, AV shunts, catheters, guide wires, balloons, and filters, which contain one or more therapeutic drugs for local administration and controlled release of such therapeutic drugs, have gained more and more acceptance in the medical device industry. These implantable medical devices (or at least portions thereof) are typically formed of or coated by a biocompatible polymer that encapsulates or otherwise contains the therapeutic drug(s), which can be released into the surrounding environment from the implantable medical devices in a controlled and sustained manner.

The biocompatible polymer as described hereinabove can be made from a polymeric solution via various different processes, including, but not limited to: spray drying (for preparation of coatings), solvent casting or spin coating (for preparation of thin films or membranes), and spinning (for preparation of fibers). The polymeric solution typically contains one or more biocompatible homopolymers or copolymers (either biostable or biodegradable) and one or more therapeutic drugs dissolved in one or more solvents.

However, the solvent(s) used in the polymeric solution may have deleterious impact on living tissues. It is therefore important to remove the solvent(s) as completely as possible from the final polymeric composition, or at least reduce the solvent content in the final polymeric composition to a safe level defined by applicable government guidelines, while without reducing the amount of therapeutic drug(s) contained therein.

For example, the polymeric solution can be coated onto or cast into at least a portion of an implantable medical device to form a drug-containing thin polymeric film (e.g., about 3 to 6 mils), and the solvent(s) contained in the polymeric film can be gradually removed by evaporation under ambient conditions (i.e., room temperature and atmospheric pressure). The final solvent content in the polymeric film typically ranges from about 5 wt % to about 10 wt %, by total weight of the film. This solvent removal method under ambient conditions results in little or no reduction of the drug content in the polymeric film.

Alternatively, the solvent(s) contained in the polymeric film can be removed by low temperature drying, which is typically carried out at temperatures ranging from about 45° C. to about 60° C. under vacuum. The low temperature drying method can remove the solvent(s) with significant efficiency, resulting in a reduced final solvent content of from about 2 wt % to about 5 wt %, with little or not reduction of the drug content in the polymeric film.

Further, the solvent(s) can be removed by high temperature drying, which is typically carried out at temperatures ranging from about 60° C. to about 110° C. The high temperature drying method can further reduce of the final solvent content in the polymeric film. However, because the therapeutic drug(s) contained in the polymeric film is typically in an amorphous state and is therefore thermally unstable, the high temperature drying method may cause degradation of the therapeutic drug(s) and lead to significant reduction of the drug content in the polymeric film.

There is therefore a continuing need for improved methods for effectively removing solvent(s) from a drug-containing polymeric composition, without removing or degrading the therapeutic drug(s) contained therein.

SUMMARY OF THE INVENTION

The present invention in one aspect relates to a method comprising:

forming a drug-containing polymeric composition comprising a biocompatible polymeric matrix with one or more therapeutic agents encapsulated therein, wherein the polymeric matrix further comprises one or more organic or aqueous solvents in an amount ranging from about 0.5 wt % to about 10 wt % of the total weight of the polymeric matrix; and treating the drug-containing polymeric composition using a low-temperature drying process at a processing temperature of less than 60° C., so as to reduce solvent content in said composition to from about 1 ppm to about 10,000 ppm.

The term "polymer" or "polymeric" as used herein refers to any material, composition, structure, or article that comprises one or more polymers, which can be homopolymers, copolymers, or polymer blends.

The term "biocompatible" as used herein refers to any material, composition, structure, or article that have essentially no toxic or injurious impact on the living tissues or living systems which the material, composition, structure, or article is in contact with and produce essentially no immunological response in such living tissues or living systems. More particularly, the material, composition, structure, or article has essentially no adverse impact on the growth and any other desired characteristics of the cells of the living tissues or living systems that are in contact with the material, composition, structure, or article. Generally, the methods for testing the biocompatibility of a material, composition, structure, or article is well known in the art.

In another aspect, the present invention relates to a drug-containing polymeric composition comprising a biocompatible polymeric matrix with one or more therapeutic agents encapsulated therein, wherein the polymeric matrix further comprises one or more organic or aqueous solvents in an amount from about 1 ppm (parts per million) to about 10,000 ppm.

The drug-containing polymeric compositions of the present invention preferably are first formed by one or more conventional processing steps to achieve a relatively low initial solvent content from about from about 0.5 wt % to about 10 wt % of the total weight of the polymeric matrix, followed by one or more low temperature processing steps to further reduce the solvent content to a range from about 1 ppm to about 10,000 ppm. By first reducing the solvent content using conventional processing steps, porosity in the final composition resulting from the low temperature drying step can be significantly reduced, while the solvent content in the final composition can be reduced to a desired level (e.g., less than 10,000 ppm), without removing the active therapeutic agents from the composition.

Conventional processing steps that can be used for forming the initial drug-containing polymeric compositions of relatively low initial solvent contents include, but are not limited to: solution processing and extrusion, melt processing using solvents and plasticizers, processing from gels and viscous solutions, solvent extraction, coating, co-extrusion, wire-coating, spinning disk, wet and dry fiber spinning, electrostatic fiber spinning, injection molding, and compression molding.

Low temperature processing steps that can be used for further reducing the solvent content in the drug-containing polymeric compositions of the present invention include, but are not limited to: lyophilization (also referred to as freeze drying), super-critical fluid extraction, and azeotropic extraction. The low temperature processes of the present invention function to increase the loading dose or concentration of drugs or other active agents in the drug-containing polymeric composition.

The drug-containing compositions of the present invention preferably comprise one or more bioabsorbable polymers and can be formed into various structures, including, but not limited to: films, fibers and tubes. The drug-containing compositions of the present invention can be readily incorporated into drug delivery devices, either as polymeric coatings or as integrated parts of the devices, for sustained and controlled local delivery of therapeutic drugs. Different geometries and performance characteristics of the drug delivery devices can be achieved, by adjusting the drug-containing polymeric compositions and/or the processing conditions used for fabricating the devices.

In a preferred but not necessary embodiment of the present invention, the drug delivery device is a stent comprised of bioabsorbable polymers with drugs or other pharmaceutically active agents incorporated therein. The drugs or other pharmaceutically active agents are incorporated into, or coated onto, the stent in significantly greater amounts than in prior art stents. Likewise, radiopaque markers may also be incorporated into or coated onto the stent, to enable visualization of the stent and thereby more precise placement of the stent in a patient's body. The delivery of greater amounts of drugs and/or other pharmaceutically active agents by the device of the present invention, in combination with the radiopaque markers, tends to improve the efficacy in treating a targeted site, disease or condition.

Other aspects, features and advantages of the invention will be more fully apparent from the ensuing disclosure and appended claims.

DETAILED DESCRIPTION OF THE INVENTION, AND PREFERRED EMBODIMENTS THEREOF

In the following description, numerous specific details are set forth, such as particular materials, compositions, formula, structures, devices, and methods for fabricating or using same, in order to provide a thorough understanding of the present invention. However, it will be appreciated by one of ordinary skill in the art that the invention may be practiced without these specific details. In other instances, well-known materials, structures or processing steps have not been described in detail in order to avoid obscuring the invention.

While specific embodiments of the present invention are described and illustrated hereinabove, it is clear that a person ordinarily skilled in the art can readily modify such specific embodiments consistent with the descriptions provided herein. It should therefore be recognized that the present invention is not limited to the specific embodiments illustrated hereinabove, but rather extends in utility to any other modification, variation, application, and embodiment, and accordingly all such other modifications, variations, applications, and embodiments are to be regarded as being within the spirit and scope of the invention.

The present invention provides several low temperature drying methods that can be used to effectively remove solvent(s) from a drug-containing polymeric composition, without removing or degrading the therapeutic drug(s) contained therein.

The drug-containing polymeric composition of the present invention preferably comprises a polymeric matrix formed by one or more biocompatible polymers (either biostable or biodegradable) with one or more therapeutic agents encapsulated therein, wherein said polymeric matrix further comprises one or more organic solvents in an amount that is from about 0.5 wt % to about 10 wt % of the total weight of the polymeric matrix. More preferably, the polymeric matrix comprises one or more organic solvents in an amount that is from about 0.5 wt % to about 5 wt %, and most preferably from about 0.5 wt % to about 2.5 wt % of the total weight of the polymeric matrix.

Such a drug-containing polymeric composition are formed from the polymeric solution as described hereinabove in the background section, by first using any one of the conventional drying methods described hereinabove, including but not limited to: solution processing and extrusion, melt processing using solvents and plasticizers, processing from gels and viscous solutions, solvent extraction, coating, co-extrusion, wire-coating, spinning disk, wet and dry fiber spinning, electrostatic fiber spinning, injection molding, compression molding, and a combination of two or more of such conventional methods.

The low temperature drying methods of the present invention are then used for further treating the drug-containing polymeric composition, to further reduce the solvent content. The low temperature drying methods of the present invention are carried out at processing temperatures of not higher than 60° C., and preferably not higher than 45° C. In this manner, the therapeutic drug(s) contained in the polymeric composition will not be degraded, and the drug content is therefore maintained at substantially the same level before and after the treatment. On the other hand, the solvent content in the drug-containing polymeric composition is reduced to less than 10,000 ppm. Preferably, the solvent content is reduced to less than 1000 ppm, more preferably to less than 100 ppm, and most preferably to less than 10 ppm, which cannot be achieved by the conventional drying methods.

In one specific embodiment of the present invention, a lyophilization method, which can also be referred to as the freeze drying method, is employed to treat the drug-containing polymeric composition, so as to further reduce the solvent content therein.

Lyophilization is a drying process achieved by freezing a liquid substance and causing the frozen substance to sublime directly to vapor by exposing it to a low partial vapor pressure. The substance may not be completely frozen, especially if non-aqueous solvents are present. However, when placed in a vacuum, the more energetic molecules will escape from the sample, causing the temperature of the sample to drop via evaporative cooling, and the sample will eventually freeze. Most of the lyophilization processes are completed by a period of desorption drying. This process is used to dry compositions that contain heat sensitive ingredients, such as drugs, therapeutic agents and biological materials. The advantages of lyophilization as a drying process include: minimum damage and loss of activity in heat-sensitive materials, speed and completeness of dehydration, and formation of porous structures.

For example, a sample material can be placed on shelves inside a drying chamber, which is first cooled to freeze the sample material at atmospheric pressure (i.e., the freezing stage), followed by creation of a vacuum for drying the sample at atmospheric temperature or at a suitable drying temperature that is above the freezing point of the solvent(s) (i.e., the drying stage). Temperature control devices can be provided to the shelves for cooling the sample material during the freezing stage and for supplying thermal energy to the sample material to compensate for the energy loss due to solvent sublimation, so as to maintain the sample material at a relatively constant drying temperature.

Typically, the solvent(s) contained in the drug-containing polymeric composition has a freezing point of about −100° C. to about 15° C. For example, dioxane has a freezing point of about 11° C.; chloroform has a freezing point of about −64° C.; acetone has a freezing point of about −95° C.; and ethyl acetate has a freezing point of about −84° C. The freeze drying method of the present invention therefore comprises the steps of first reducing the temperature of the drug-containing polymeric composition to near the freezing point of the solvent(s), then placing the drug-containing polymeric composition in a vacuum at a pressure of less than 4 torr, followed by raising the temperature of the drug-containing polymeric composition to significantly above the freezing point of the solvent(s), but typically below 60° C., and preferably below 45° C.

In this manner, the solvent(s) in the drug-containing polymeric composition is first frozen into a solid state, which is then removed by sublimation under the vacuum condition.

Preferably, rapid cooling techniques are employed to reduce the temperature of the drug-containing polymeric composition to below the freezing point of the solvent(s). Rapid cooling minimizes the deleterious impact on the therapeutic potency of the drug(s) contained in the polymeric composition.

In another specific embodiment of the present invention, a supercritical extraction method is employed to further treat the drug-containing polymeric composition and further reduce the solvent content therein.

At a thermodynamic state above the critical temperature ($T_c$) and critical pressure ($P_c$), gases can exist as supercritical fluids (SCFs), which exhibit a number of unique properties. The critical points represent the highest temperature and pressure at which the substance can exist as a vapor and liquid in equilibrium. SCFs exhibit properties that are in between those of liquids and gases. Some of the characteristics of supercritical fluids include: density and solubility approaching liquid phase, and diffusivity approaching gas phase. By operating in the critical density region, pressure and temperature can be used to regulate density, solubility, and diffusivity of the SCFs. Mass transfer is rapid with supercritical fluids, and their dynamic viscosities are closer to those found in normal gaseous states. In the region of the critical points, the diffusion coefficient is more than ten times that of a liquid. Viscosity and diffusivity are also dependent on temperature and pressure, and the changes in viscosity and diffusivity are more pronounced in the region of the critical points. Therefore, the properties of gas-like diffusivity, gas-like viscosity, and liquid-like density combined with pressure-dependent solvating power have provided the opportunity for applying supercritical fluid technology to solve problems in various areas. SCFs exhibit high solvent power for many normally insoluble substances and therefore can be used for extraction of specific substances from liquid and solid mixtures. SCFs have been used for decaffeination of coffee, removal of saturated fats and cholesterol from snacks and food products, dry cleaning of clothes, and detecting the presence of pesticides in crops.

Commonly used materials for forming SCFs include carbon dioxide, ethane, water, ammonia, isopropanol, acetone, and their mixtures. Specifically, the use of carbon dioxide has attracted significant attention, due to its non-toxic, non-flammable, and chemically inert characteristics as well as its availability and relatively inexpensiveness. Super critical conditions for carbon dioxide can be easily attained at a pressure of 73.8 bar and a temperature of 31.1° C. Other advantages of using carbon dioxide are that: (1) the solvent(s) can be removed by simple depressurization, (2) the density of the solvent(s) can be tuned by varying the pressure, and (3) many polymers become highly swollen and plasticized in the presence of carbon dioxide. Supercritical carbon dioxide has therefore been widely used in polymer synthesis and polymer processing, due to these advantages.

In the present invention, a supercritical extraction fluid, such as supercritical carbon dioxide, is used to extract the solvent(s) from the drug-containing polymeric composition at a temperature below 60° C., and more typically below 45° C., and a pressure ranging from about 10 bars to 500 bars. Preferably, the supercritical extraction is carried out at a temperature ranging from about 25° C. to about 40° C. and a pressure ranging from about 50 bars to about 150 bars.

In still another specific embodiment of the present invention, an azeotropic extraction method is employed to treat the drug-containing polymeric composition, so as to further reduce the solvent content therein.

Specifically, an azeotrope, which contains solvents such as dioxane and chlorinated solvents, is added to the drug-containing polymeric composition. An azeotrope is a liquid mixture of two or more substances. It behaves like a single substance in that the vapor produced by partial evaporation of liquid has the same composition as the liquid. Preferably, the azeotrope contains a mixture of two solvents, i.e., a binary azeotrope. Further, the azeotrope is a minimum-boiling azeotrope where the boiling point of the mixture is lower than the boiling point of either component. The azeotrope is miscible with the solvent(s) contained in the drug-containing polymeric composition, so that the solvent(s) can be extracted together with the azeotrope by evaporation at lower temperatures.

The above-described low temperature drying methods are used in combination with and subsequent conventional drying methods, to achieve desired low solvent content in the final drug-containing polymeric composition. As mentioned hereinabove, the conventional drying methods are carried out first to reduce the solvent content to a relatively low initial level (e.g., from about 0.5 wt % to about 10 wt %), and the low temperature drying methods are then carried out to further reduce the solvent content to a significantly level range (i.e., from about 1 ppm to about 10,000 ppm) that cannot be achieved by the conventional drying methods. The initial solvent reduction functions to prevent formation of significant porosity under the low temperature drying conditions.

According to the systems and methods of the invention, a drug delivery device comprised of bioabsorbable materials that incorporates one or more therapeutic agents at an sufficient amount and has a solvent content ranging from about 1 ppm to about 10,000 ppm can be made by any of a variety of processes. The drug delivery devices can be prepared by solution-based processes using solvents as by, for example, fiber spinning (dry and wet spinning), electrostatic fiber spinning, spinning disk (thin films with uniform thickness), extrusion and co-extrusion, co-mingled fibers, solvent cast films, or solvent cast tubes, wherein a drying process that combines both conventional drying methods and low temperature drying methods is used to remove solvents after the drug delivery devices are formed. The artisan should readily appreciate the general techniques attendant with the various methods referred to above and, except as otherwise provided herein, detailed explanations thereof are omitted for brevity but understood to be included herein.

The processes used to prepare the drug delivery devices are preferably low temperature processes, in order to minimize degradation of drugs or other therapeutic agents that are incorporated into the matrix of bioabsorbable polymeric materials comprising the devices. To this end, processing methods may comprise forming the device from bioabsorbable polymeric materials by using low temperature, solution-based processes, as outlined above and discussed in greater detail further below.

The drug delivery devices of the present invention can be disease specific, and they can be designed for local or regional therapy, or a combination thereof. The drugs or other agents delivered by the drug delivery devices according to the systems and methods of the invention may be one or more drugs, bio-active agents such as growth factors or other agents, or combinations thereof. The drugs or other agents of the device are ideally controllably released from the device, wherein the rate of release depends on either or both of the degradation rates of the bioabsorbable polymers forming the device and the nature of the drugs or other agents. The rate of drug release can vary widely from a few minutes to a few years as desired.

Any suitable biocompatible polymer, copolymer, or polymer blend can be used for forming the polymeric composition or drug delivery devices of the present invention. Such biocompatible polymer, copolymer, or polymer blend may either be biostable or bioabsorbable. Biostable polymers that are suitable for use in this invention include, but are not limited to: polyurethane, silicones, polyesters, polyolefins, polyamides, poly(esteramide), polycaprolactam, polyimide, polyvinyl chloride, polyvinyl methyl ether, polyvinyl alcohol, acrylic polymers and copolymers, polyacrylonitrile; polystyrene copolymers of vinyl monomers with olefins (such as styrene acrylonitrile copolymers, ethylene methyl methacrylate copolymers, ethylene vinyl acetate), polyethers, rayons, cellulosics (such as cellulose acetate, cellulose nitrate, cellulose propionate, etc.), parylene and derivatives thereof; and mixtures and copolymers of the foregoing. Bioabsorbable polymers that can be used in this invention include, but are not limited to: poly(L-lactic acid), poly(DL-lactic acid), polycaprolactone, polyglycolide, poly(dioxanone); copolymers such as poly (lactide-co-glycolide), poly(hydroxy butyrate-co-valerate), poly(glycolide-co-trimethylene carbonate); polyphosphoester; poly(phosphoester-urethane); poly(amino acids); biomolecules such as fibrin, fibrinogen, cellulose, starch, collagen and hyaluronic acid; and mixtures and copolymers Surface erosion polymers or bulk erosion polymers, for example, can also be used as the bioabsorbable polymer in order to better control the drug delivery therefrom.

Surface erosion polymers are typically hydrophobic with water labile linkages. Hydrolysis tends to occur fast on the surface of such surface erosion polymers with no water penetration in bulk. The drug release rate from devices comprised of such surface erosion polymers can thus be varied linearly while maintaining the mechanical integrity of the device. The initial strength of such surface erosion polymers tends to be low however, and often such surface erosion polymers are not readily available commercially. Nevertheless, examples of surface erosion polymers that could be used to help vary the drug delivery rate of a device according to the systems and methods of the invention include polyanhydrides, such as poly (carboxyphenoxy hexane-sebacic acid), poly (fumaric acid-sebacic acid), poly (carboxyphenoxy hexane-sebacic acid), poly (imide-sebacic acid)(50-50 ratio), poly (imide-carboxyphenoxy hexane)(33-67 ratio), and polyorthoesters (e.g., diketene acetal based polymers).

Bulk erosion polymers, on the other hand, are typically hydrophilic with water labile linkages. Hydrolysis of bulk erosion polymers tends to occur at more uniform rates across the polymer matrix of the device. As a result, bulk erosion polymers release initial bursts of drugs during breakdown of the polymer matrix. Bulk erosion polymers exhibit superior initial strength and are readily available commercially. Examples of bulk erosion polymers usable with the drug delivery devices according to the system and methods of the invention include: poly ($\alpha$-hydroxy esters), such as poly (lactic acid), poly (glycolic acid), poly (caprolactone), poly (p-dioxanone), poly (trimethylene carbonate), poly (oxaesters), poly (oxaamides), and their co-polymers and blends. Some commercially available bulk erosion polymers and their commonly associated medical applications include: poly (dioxanone) [PDS® suture available from Ethicon, Inc., Somerville, N.J.], poly (glycolide) [Dexon® sutures available from United States Surgical Corporation, North Haven, Conn.], poly (lactide)-PLLA [for bone repair], poly (lactide/glycolide) [Vicryl® (10/90) and Panacryl® (95/5) sutures available from Ethicon, Inc., Somerville, N.J.], poly (glycolide/caprolactone (75/25) [Monocryl® sutures available from Ethicon, Inc., Somerville, N.J.], and poly (glycolide/trimethylene carbonate) [Maxon® sutures available from United States Surgical Corporation, North Haven, Conn.]. Other bulk erosion polymers can also be used to form the drug delivery devices of the present invention. For example, tyrosine-derived polypeptides [e.g., poly (DTH carbonates), poly (arylates), and poly (imino-carbonates)], phosphorous containing polymers [e.g., poly (phosphoesters) and poly (phosphazenes)], poly (ethylene glycol) [PEG] based block co-polymers [PEG-PLA, PEG-poly (propylene glycol), PEG-poly (butylene terphthalate)], poly ($\alpha$-malic acid), poly (ester amide), and polyalkanoates [e.g., poly (hydroxybutyrate (HB) and poly (hydroxyvalerate) (HV) co-polymers] can also be used.

Of course, according to the systems and methods of the invention, the drug delivery devices may be made from combinations of surface and bulk erosion polymers, in order to achieve desired physical properties and to control the degradation mechanism and drug release therefrom as a function of time. For example, two or more polymers may be blended in order to achieve desired physical properties, device degradation rate and drug release rate. Alternatively, the drug delivery device can be made from a bulk erosion polymer that is coated with a drug-containing surface erosion polymer. Further, the drug-containing polymer coating can be sufficiently thick that high drug loads can be achieved, and the bulk erosion polymer may be made sufficiently thick that the mechanical properties of the device are maintained, even after all of the drug has been delivered and the surface eroded.

While the degradation and drug release factors are considered in choosing the bioabsorbable polymers for forming the drug delivery devices of the present invention, maintaining the mechanical integrity and resilience of the devices is also an important factor to be considered. In this regard, shape memory polymers can be employed to help a device maintain, or remember, its original shape after deployment of the device into a patient's body.

Shape memory polymers are characterized as phase segregated linear block co-polymers having a hard segment and a soft segment. The hard segment is typically crystalline with a defined melting point, and the soft segment is typically amorphous with a defined glass transition temperature. The transition temperature of the soft segment is substantially less than the transition temperature of the hard segment in shape memory polymers. A shape in the shape memory polymer is memorized in the hard and soft segments of the shape memory polymer by heating and cooling techniques in view of the respective transition temperatures, as the artisan should appreciate.

Shape memory polymers can be biostable and bioabsorbable. Bioabsorbable shape memory polymers are relatively new and include thermoplastic and thermoset materials. Shape memory thermoset materials may include poly (caprolactone) dimethylacrylates, and shape memory thermoplastic materials may include poly (caprolactone) as the soft segment and poly (glycolide) as the hard segment.

Selection of the bioabsorbable polymeric material for forming the drug delivery device of the present invention can be readily determined based on many factors including, for example, the desired absorption times and physical properties of the bioabsorbable materials, and the geometry of the drug delivery device.

In order to provide materials having high ductility and toughness, as is often required for orthopedic implants, sutures, stents, grafts and other medical applications including drug delivery devices, the bioabsorbable polymeric materials may be modified to form composites or blends thereof. Such composites or blends may be achieved by mixing the polymeric materials with different polymers and plasticizers. Plasticizers, such as low molecular weight poly(ethylene glycol), poly(caprolactone), and citrate esters can be used. Any additional materials used to modify the underlying bioabsorbable polymer should preferably be compatible with the main polymer system. The additional materials also tend to depress the glass transition temperature of the bioabsorbable polymer, which renders the underlying polymer more ductile and less stiff.

As an example of producing a composite or blended material for the drug delivery device, blending a very stiff polymer, such as poly (lactic acid), poly (glycolide) and poly (lactide-co-glycolide) copolymers, with a soft and ductile polymer, such as poly (caprolactone) and poly(dioxanone), tends to produce a material with high ductility and high stiffness. An elastomeric co-polymer can also be synthesized from a stiff polymer and a soft polymer in different ratios. For example, poly(glycolide) or poly(lactide) can be copolymerized with poly(caprolactone) or poly(dioxanone) to prepare poly(glycolide-co-caprolactone) or poly(glycolide-co-dioxanone) and poly(lactide-co-caprolactone) or poly(lactide-co-dioxanone) copolymers. These elastomeric copolymers can then be blended with stiff materials such as poly(lactide), poly (glycolide) and poly(lactide-co-glycolide) copolymers, to produce a material with high ductility. Alternatively, terpolymers can also be prepared from different monomers to achieve desired properties. Macromers and other cross-linkable polymer systems can be used to achieve the desired properties. Such properties are conducive to a drug delivery stent device according to systems and methods of the invention. Of course, the underlying polymer could also be blended with a stiffer polymer to produce a material having stiffer properties, as might be useful in the case of an orthopedic implant having growth factors or other bio-active agents or drugs delivered therefrom according to the systems and methods of the invention.

The drugs or other bio-active agents delivered by the drug delivery devices according to the systems and methods of the invention may include rapamycin, statins and taxol, or any suitable other drugs or bio-active agents. The drugs or other bio-active agents may be used to treat various diseases, such as restenosis, vulnerable plaque, angina and ischemic stroke. More specifically, such drugs or bio-active agents can be incorporated into or coated onto a stent for treatment of such diseases. Growth factors, such as fibro-blasts and vascular endothelial growth factors, can also be used in lieu of, or together with, the drugs. Such growth factors may be used for angiogenesis, for example.

In addition to the various drugs identified above, the drugs or other agents incorporated into the device can also include cytostatic and cytotoxic agents, such as, heparin, everolimus, tacrolimus, biolimus, paclitaxel, statins and cladribine. The various drugs or agents can be hydrophobic or hydrophilic as appropriate. In some of the examples set forth below, sirolimus was the drug incorporated into the drug delivery devices.

Other drugs or other bio-active agents usable with the drug delivery devices made according to the systems and methods described herein include: antiproliferative/antimitotic agents including natural products such as vinca alkaloids (i.e., vinblastine, vincristine, and vinorelbine), paclitaxel, epidipodophyllotoxins (i.e., etoposide, teniposide), antibiotics (dactinomycin (actinomycinD) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagines); antiplatelet agents such as G(GP) $11_b/111_a$ inhibitors and vitronectin receptor antagonists; anti-proliferative/antimitotic alkylating agents such as nitrogen mustards (mechlorethamine, cyclophosphamide and anolgs, melphalan, chlorambucil), ethylenimines and methylmelamines (hexamethylmelamine and thiotepa), alkyl sulfonaates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (flourouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, arninglutethimide; hormones (i.e., estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6 α-methylprednisolone, triamcinolone, betamethasone, and dexamethasone), nonsteroidal agents (salicylic acid derivatives i.e., aspirin; para-aminphenol derivatives i.e., acetominophen; indole and indene acetic acids (indomethacin, sulindac, and etodalac), heteroaryl acetic acids (tolmetin, diclofenac, and ketorolac), arylpropionic acids (tomfetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate (mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The amount of drugs or other agents incorporated within the drug delivery device according to the systems and methods of the invention can range from 0 to 99% by the total weight of the device. The drugs or other agents can be incorporated into the device in different ways. For example, the drugs or other agents can be coated onto the device after the device has been formed, wherein the coating is comprised of bioabsorbable polymers into which the drugs or other agents are incorporated. Alternatively, the drugs or other agents can be incorporated into the matrix of bioabsorbable materials comprising the device. The drugs or agents incorporated into the matrix of bioabsorbable polymers can be in an amount the same as, or different from, the amount of drugs or agents provided in the coating techniques discussed earlier if desired. These various techniques of incorporating drugs or other agents into, or onto, the drug delivery device may also be combined to optimize performance of the device, and to help control the release of the drugs or other agents from the device.

Where the drug or agent is incorporated into the matrix of bioabsorbable polymers comprising the device, for example, the drug or agent will release by diffusion and during degradation of the device. The amount of drug or agent released by diffusion will tend to release for a longer period of time than occurs using coating techniques, and can often more effectively treat local and diffuse lesions or conditions therefore. For regional drug or agent delivery such diffusion release of the drugs or agents is effective as well.

The drug delivery device according to the systems and methods of the invention preferably retains its mechanical integrity during the active drug delivery phase of the device. After drug delivery is achieved, the structure of the device ideally disappears as a result of the bioabsorption of the materials comprising the device. The bioabsorbable materials comprising the drug delivery device are preferably biocompatible with the tissue in which the device is implanted such that tissue interaction with the device is minimized even after the device is deployed within the patient. Minimal inflammation of the tissue in which the device is deployed is likewise preferred even as degradation of the bioabsorbable materials of the device occurs.

Because visualization of the drug delivery device as it is implanted in the patient is helpful to the medical practitioner for locating and orienting the device, and for maximizing the dispersal of the drugs or other agents to an intended site once implanted, radiopaque materials may be added to the device. The radiopaque materials may be added directly to the matrix of bioabsorbable materials comprising the device during processing thereof, resulting in fairly uniform incorporation of the radiopaque materials throughout the device. Alternatively, the radiopaque materials may be added to the device in the form of a layer, a coating, a band or powder at designated portions of the device, depending on the geometry of the device and the process used to form the device.

Ideally, the radiopaque material does not add significant stiffness to the drug delivery device so that the device can readily traverse the anatomy within which it is deployed. The radiopaque material should be biocompatible with the tissue within which the device is deployed. Such biocompatibility minimizes the likelihood of undesirable tissue reactions with the device. Inert noble metals such as gold, platinum, iridium, palladium, and rhodium are well-recognized biocompatible radiopaque materials. Other radiopaque materials include barium sulfate ($BaSO_4$), bismuth subcarbonate ($(BiO)_2CO_3$), bismuth oxide, tungsten, tantalum, and iodine compounds, at least some of which are used in examples described further below. Ideally, the radiopaque materials adhere well to the device such that peeling or delamination of the radiopaque material from the device is minimized, or ideally does not occur.

Where the radiopaque materials are added to the device as metal bands, the metal bands may be crimped at designated sections of the device. Alternatively, designated sections of the device may be coated with a radiopaque metal powder, whereas other portions of the device are free from the metal powder. As the artisan should appreciate, barium is most often used as the metallic element for visualizing the device using these techniques, although tungsten and other fillers are also becoming more prevalent.

Radiopaque coatings on all or portions of the device can also be used to enhance the radiopacity and visualization of the device deployed within the patient. Such coatings sometimes have less negative impact on the physical characteristics (e.g., size, weight, stiffness, flexibility) and performance of the device than do other techniques. Coatings can be applied to the device in a variety of processes known in the art such as, for example, chemical vapor deposition (CVD), physical vapor deposition (PVD), electroplating, high-vacuum deposition process, microfusion, spray coating, dip coating, electrostatic coating, or other surface coating or modification techniques.

Alternatively, the bioabsorbable polymer materials used to comprise the drug delivery device according to the invention can include radiopaque additives added directly thereto during processing of the matrix of the bioabsorbable polymer materials to enhance the radiopacity of the device. The radiopaque additives can include inorganic fillers, such as barium sulfate, bismuth subcarbonate, bismuth oxides and/or iodine compounds. The radiopaque additives can instead include metal powders such as tantalum or gold, or metal alloys having gold, platinum, iridium, palladium, rhodium, a combination thereof, or other materials known in the art. The particle size of the radiopaque materials can range from nanometers to microns, and the amount of radiopaque materials can range from 0-99% (wt %).

Because the density of the radiopaque additives is typically very high where the radiopaque materials are distributed throughout the matrix of bioabsorbable materials, dispersion techniques are preferably employed to distribute the radiopaque additives throughout the bioabsorbable materials as desired. Such techniques include high shear mixing, surfactant and lubricant additions, viscosity control, surface modification of the additive, and other particle size, shape and distribution techniques. In this regard, it is noted that the radiopaque materials can be either uniformly distributed throughout the bioabsorbable materials of the device, or can be concentrated in sections of the device so as to appear as markers similar to as described above.

Preferred low temperature processes of forming the drug delivery devices according to the systems and methods of the invention include solution processing and supercritical fluid processing techniques. These processes include solvent extraction, coating, wire-coating, extrusion, co-extrusion, fiber-spinning including electrostatic fiber-spinning, lyophilization, azeotropic extraction and other techniques that incorporate drugs or other bio-active agents that are unstable at high temperatures into the matrix of bioabsorbable polymeric materials that will comprise the drug delivery device. For drugs or agents that are stable at high temperature, different melt processing techniques may instead be used to incorporate the drugs or agents into the matrix of bioabsorbable polymers that comprise the device. Alternatively, the drugs or agents may be sprayed, dipped, or coated onto the device after formation thereof from the bioabsorbable polymers. In either case, the polymer matrix, and drug or agent blend when provided, is then converted into a structure such as fibers, films, discs/rings or tubes, for example, that is thereafter further manipulated into various geometries or configurations as desired.

Different processes can thus provide different structures, geometries or configurations to the bioabsorbable polymer being processed. For example, tubes processed from rigid polymers tend to be very stiff, but can be very flexible when processed via electrostatic processing or lyophilization. In the former case, the tubes are solid, whereas in the latter case, the tubes are porous. Other processes provide additional geometries and structures that may include fibers, microfibers, thin and thick films, discs, foams, microspheres and even more intricate geometries or configurations. Melt or solution spun fibers, films and tubes can be further processed into different designs such as tubular, slide and lock, helical or otherwise by braiding and/or laser cutting. The differences in structures, geometries or configurations provided by the different processes are useful for preparing different drug delivery devices with desired dimensions, strengths, drug delivery and visualization characteristics.

Different processes can likewise alter the morphological characteristics of the bioabsorbable polymer being processed. For example, when dilute solutions of polymers are stirred rapidly, the polymers tend to exhibit polymer chains that are generally parallel to the overall axis of the structure. On the other hand, when a polymer is sheared and quenched to a thermally stable condition, the polymer chains tend to elongate parallel to the shear direction. Still other morphological changes tend to occur according to other processing techniques. Such changes may include, for example, spherulite to fibril transformation, polymorphic crystal formation change, re-orientation of already formed crystalline lamellae, formation of oriented crystallites, orientation of amorphous polymer chains and/or combinations thereof.

In the case of a drug delivery device comprised of bioabsorbable polymeric materials according to the systems and method of the invention, the device may be formed by solution spinning fibers or solvent cast films or tubes, for example, wherein the polymer fibers, films or tubes are typically formed at ambient conditions. As a result, drugs incorporated therein the bioabsorbable polymeric materials do not degrade as readily. After formation, the fibers, films or tubes are laser cut to a desired geometry or configuration such as in the shape of a stent.

Examples, as set forth below, describe solvent-cast films and tubes prepared from bioabsorbable polymeric materials for use in drug delivery devices, wherein the bioabsorbable polymeric materials are selected from polylactide/polyglycolide copolymers such as PLA/PGA (95/5 and 85/15), and blends thereof. Polymeric blends were prepared to make stiff polymers more ductile and flexible in order to prepare stents that require more strain values. Different solvents, such as chloroform, dioxane, and binary solvent mixtures, such as dioxane/acetone and dioxane/ethyl acetate, were used to prepare the films. Different radiopaque agents were used from 10% to 40% (by weight) from materials including barium sulfate, bismuth subcarbonate, bismuth oxide, tungsten and tantalum. Sirolimus was provided as the therapeutic agent in these films and tubes at concentrations ranging from 5 to 30% (by weight).

Typically, one or more bioabsorbable polymers and therapeutic agents, and optionally radiopaque markers, are added to a given solvent, mixed and tumbled, with or without heat, until the polymer(s) and the therapeutic agent(s), and optionally the radiopaque markers, dissolve completely in the solvent to provide a homogenous solution.

Drug-containing polymeric compositions can then be prepared from such a solution.

For example, the solution can be converted to drug-containing polymeric films by pouring it into a mold or onto a glass plate, and allowing the solvent to evaporate overnight in a nitrogen rich environment at room temperature. The film is then removed from the glass plate and treated by a low-temperature drying method as described hereinabove to further reduce the solvent content contained therein.

Alternatively, the solution can be used to prepare solvent cast tubes, by depositing the solution onto a mandrel at room or higher temperature. The mandrel may be coated, for example with Teflon, to improve eventual removal therefrom. A syringe pump, for example, may be used to deposit the polymer solution onto the mandrel. The mandrel is then dried. The mandrel may be dried in a solvent rich environment and/or a nitrogen rich environment. The tube may then be removed and the solvent can be further removed under different conditions.

Other geometries and configurations, such as melt and solvent extruded tubes, foams, fibers, discs, stents, etc., can also be prepared by the methods of the present invention.

The drug-containing polymeric compositions prepared from the solutions described hereinabove are first treated by a conventional drying methods, such as high temperature oven drying (e.g., at 80° C. to 110° C. for about 10 hours) and low temperature oven drying (e.g., at 25° C. to 80° C. for about 10 hours), followed by treatment by a low temperature drying method as described hereinabove, such as supercritical carbon dioxide extraction (e.g., at a temperature of about 25-60° C. and a pressure of about 60 to 80 bars for 20 to 60 minutes), lyophilization, azeotropic extraction, or a combination thereof. Low temperature drying is used to preserve drug content in the films. The drying conditions will also determine the morphology (amorphous or crystalline) of the films and tubes.

The main objective of this invention is to extract residual solvent(s) from polymer films and tubes loaded with rapamycin without significant loss of the drug. A combination approach using conventional thermal drying followed by supercritical carbon dioxide extraction was used to remove solvent from drug containing bioabsorbable films and tubes to prepare stents. The supercritical extraction conditions can include a range for different processing parameters, depending on the vessel size, the experimental set-up, the sample size, and the geometry. Specifically, the processing temperature can range from about 35° C. to 50° C.; the processing pressure can range from about 60 bars to about 500 bars. The carbon dioxide flow rate can range from about 1 g/min to about 200 g/min, and the processing time can range from about 10 to 200 minutes.

Example I

Films were prepared from PLGA 95/5 from chloroform that contained 15% rapamycin and 20% barium sulfate. The films were dried at 45° C. in nitrogen. Another film was cast from 1,4-dioxane solution of the same polymer with no drug or barium sulfate. Both films contained significant amount of residual solvent before extraction.

The system used for the extraction study was a supercritical fluid system equipped with a photodiode array UV detector. A film sample was first loaded into an extraction cell (a 25 ml cell was used in this case) and then placed into the system for extraction using supercritical $CO_2$ under very mild conditions. The $CO_2$ exiting the cell was introduced into the UV detector to detect drug and solvent absorbance. The extraction conditions were 35° C. at 77 bars. The drug and solvent absorbance were monitored on-line.

Table I below summarizes the extraction conditions and analytical results.

TABLE 1

| Film | Extraction Time (min) | Sample weight (g) Before | Sample weight (g) After | Weight Loss % | Solvent content Before (%) | Solvent content After (ppm) | Drug content Before (%) | Drug content After (%) |
|---|---|---|---|---|---|---|---|---|
| PLGA 95/5, barium sulfate and sirolimus (chloroform) | 100 | 0.5982 | 0.5631 | 5.9 | 6.1 | 30 | 15.70 | 14.28 |
| PLGA 95/5 (dioxane) | 40 | 0.3510 | 0.3329 | 5.2 | 7 | 35 | N/A | N/A |

These results show that the solvent can be easily extracted from the films by using supercritical carbon dioxide, without significant loss of the drug. The final solvent contents in the polymeric compositions were less than 50 ppm, which cannot be achieved by conventional drying methods.

It should be noted that the extraction conditions used were set at low temperature and low pressure. These process conditions (temperature, pressure, time, extraction cell volume, etc) can be optimized to achieve rapid and complete removal of the solvent(s) while minimize drug loss.

Example II

Several films were prepared from PLGA 95/5 with no additives, or with 20% barium sulfate, or with 20% barium sulfate and 15% sirolimus from dioxane and chloroform. All these films were prepared by casting in a mold, and then purged with nitrogen for 20 hours at ambient temperature, followed by thermal drying at 45° C. for 20 h with nitrogen purge. The table below summarizes all the compositions of the films that were prepared for the extraction study.

TABLE 2

| | % by Weight | | |
|---|---|---|---|
| Sample ID | Sirolimus | PLA-PGA | Barium sulfate |
| 4-1-A | 14.79 | 85.21 | 0 |
| 4-2-A | Pure PLA-PGA cast from chloroform | | |
| 4-3-A | | | |
| 4-4-A | 14.87 | 85.13 | 0 |
| 4-5-A | Pure PLA-PGA cast from dioxane | | |
| 4-6-A | | | |
| 5-1-A | 14.68 | 66.7 | 18.55 |
| 5-2-A | 0 | 78.33 | 21.67 |
| 5-3-A | 0 | 78.33 | 21.67 |
| 6-4-A | 14.70 | 66.80 | 18.50 |
| 6-5-A | 0 | 78.35 | 21.65 |
| 6-6-A | 0 | 78.35 | 21.65 |
| 4-4 | 14.87 | 85.13 | 0 |
| 4-6 | Pure PLA-PGA cast from dioxane | | |
| 5-1 | 14.68 | 66.7 | 18.55 |
| 5-2 | 0 | 78.33 | 21.67 |
| 6-4 | 14.70 | 66.80 | 18.50 |

Solvent removal from the polymer films was then carried out using the following steps:

(1) The polymer was first weighed and placed inside a high-pressure extraction column.

(2) The high-pressure column was then pressurized at up to the operating pressure and temperature of 80 bars and 35° C. respectively using supercritical $CO_2$ ($scCO_2$). Extraction of solvent was carried out using a constant stream of $scCO_2$ at 2 g/min.

(3) The exhaust from the extraction column was monitored for solvent content in a continuous manner using a photo diode array (PDA) detector. This was done in order to study the rate and the amount of loss of solvent from the film sample.

(4) Once the required level of solvent loss was achieved the flow of $scCO_2$ was terminated, the high-pressure extraction column was depressurized and the polymer film samples were collected for analysis.

The results of the extraction experiments have been summarized in the tables below. Efficient solvent extraction was achieved in all cases as indicated by the PDA detector. Changing appropriate parameters such as the extraction pressure, temperature, extraction time and flow rate can further optimize the extraction conditions.

TABLE 3

Polymer Film Extraction
Using $scCO_2$ at 80 bars, 35° C. and 2 g/min $CO_2$ flow rate

| Expt. No. | Sample ID | $W_o$ | Time | Comments |
|---|---|---|---|---|
| 1 | 4-6 | 1.1656 g | 93 minutes | Almost all residual dioxane in film removed |
| 2 | 5-2 | 1.4568 g | 60 minutes | Almost all residual dioxane removed |
| 3 | 4-4 | 1.4738 g | 150 minutes | Almost all of the residual solvent in film removed. |
| 4 | 6-4 | 2.0878 g | 60 minutes | Almost all of the residual solvent in film removed |
| 5* | 5-1 | 1.7835 g | 37 minutes | Almost all of the residual solvent in film removed. |

* Operating pressure at 75 bars and $CO_2$ flow rate of 1 g/min
$W_0$ - Initial weight of polymer film before extraction
Time - Extraction time

TABLE 4

Sirolimus and Residual Solvent Content in Films Before and After Extraction

| Sample ID | Residual Solvent (ug/g) | Sirolimus (%) | | | |
|---|---|---|---|---|---|
| | | Found in film | Corrected for Residual Solvent [1] | Theoretical (%) | Recovery [2] (%) |
| 4-1-A | 98301 (C) [4] | 12.03 | 13.34 | 14.8 | 90.2 |
| 4-2-A | 76861 (C) | | N/A [3] | | |
| 4-3-A | 79286 (C) | | | | |
| 4-4-A | 81897 (D) | 5.47 | 5.96 | 14.9 | 40.1 |
| 4-5-A | 76042 (D) | | N/A | | |
| 4-6-A | 79608 (D) | | | | |
| 5-1-A | 71911 (D) | 6.74 | 7.26 | 14.7 | 49.5 |
| 5-2-A | 59956 (D) | | | | |
| 5-3-A | 64154 (D) | | | | |
| 6-4-A | 83487 (C) | 12.87 | 14.04 | 14.7 | 95.5 |
| 6-5-A | 64639 (C) | | N/A | | |
| 6-6-A | 68860 (C) | | | | |
| 4-4 (dried) | 105 (D) | 6.45 | 6.45 | 14.9 | 43.4 |
| 4-6 (dried) | 391 (D) | | N/A | | |
| 5-1 (dried) | 2193 (D) | 7.48 | 7.50 | 14.7 | 51.1 |
| 5-2 (dried) | 127 (D) | | N/A | | |
| 6-4 (dried) | 422 (C) | 10.30 | 10.30 | 14.7 | 70.1 |

[1] Corrected = Found/[(100 − % Residual solvent)/100]
[2] Recovery calculated based on sirolimus theoretical values (from the film preparation data).
[3] N/A: Not Available
[4] (C): Chloroform, (D): Dioxane The results show that after supercritical extraction, residual solvent has been lowered significantly (to less than 10,000 ppm) with high drug recovery rates.

Example III

Experiments for this study were conducted for PLGA 95/5 films with 20% barium sulfate and 15% sirolimus prepared from chloroform and stabilized dioxane. Two different drying conditions were used, namely, 60° C. for 6 hours and ramping drying at 50° C., 70° C., and 90° C. for 2 hours at each temperature. After this drying, films were extracted using supercritical carbon dioxide under different conditions as described below. The films used are summarized in the table below.

TABLE 5

| Sample ID | Description |
|---|---|
| 20-1 | PLA-PLG (95:5) with BaSO$_4$ and drug cast from |
| 20-2 | Chloroform. Dried at 60° C. for 6 h. Film thickness |
| 20-3 | is 6 mils |
| 20-4 | |
| 20-5 | |
| 21-1 | PLA-PGA (95:5) with BaSO$_4$ and drug cast from Stabilized |
| 21-3 | Dioxane. Dried at 60° C. for 6 h. Film thickness is 4 mils |
| 21-4 | |
| 21-5 | |
| 21-6 | |
| 22-1 | PLA-PGA (95:5) with BaSO$_4$ and drug cast from Stabilized |
| 22-2 | Dioxane. Ramping experiment: Dried at 50° C. for 2 h, 70° C. |
| 22-3 | for 2 h, and 90° C. for 2 h. Film thickness is 4 mils. |

Sirolimus and residual solvents content in films after film preparation is summarized below:

TABLE 6

| Sample ID | Residual Solvents (ug/g) | Sirolimus | | |
|---|---|---|---|---|
| | | Found in Film (%) | Corrected | Recovery |
| 20-1 | 82928 (C) | 14.30 | 15.59 | 104.3 |
| 20-4 | 88624 (C) | 13.56 | 14.88 | 99.5 |
| 21-3 | 21273 (D) | 14.69 | 15.01 | 100.4 |
| 21-4 | 28735 (D) | 14.27 | 14.69 | 98.3 |
| 22-1 | 2337 (D) | 13.57 | 13.60 | 91.0 |
| 22-3 | 1682 (D) | 13.45 | 13.47 | 90.1 |

These films were extracted in a supercritical CO$_2$ chromatography system using a 25 ml vessel. Each film was cut into small specimens and extracted at 35° C. and 77 bars for different times (A-20 minutes; B-60 minutes; C-100 minutes and D-140 minutes). The nominal CO$_2$ flow rate was 2 g/min. The actual conditions for different samples are summarized as follows:

TABLE 7

Extraction temperature: 35° C., pressure: 77 Bar for all samples

| Sample ID | Extraction Time (min) | CO$_2$ flow rate (g/min) | Sample Weight (g) | | |
|---|---|---|---|---|---|
| | | | Before | After | % Change |
| 22-1-A | 20 | 2 | 0.3403 | 0.3263 | 4.3 |
| 22-1-B | 60 | 2 | 0.3239 | 0.3116 | 3.9 |
| 22-1-C | 100 | 2 | 0.3061 | 0.2993 | 2.3 |
| 22-1-D | 140 | 1 | 0.3411 | 0.3339 | 2.2 |
| 20-1-A | 20 | 2 | 0.3541 | 0.3401 | 4.1 |
| 20-1-B | 60 | 2 | 0.4393 | 0.4001 | 9.8 |
| 20-1-C | 100 | 2 | 0.4439 | 0.4025 | 10.3 |
| 21-4-A | 20 | 2 | 0.2928 | 0.2834 | 3.3 |
| 21-4-B | 60 | 2 | 0.3351 | 0.3238 | 3.5 |

The drug and residual solvent analyses results are listed in the following table.

TABLE 8

Drug Content and Residual Solvent (After Extraction)

| Sample ID | Sirolimus (%) | Residual chloroform(ppm) | Residual Dioxane(ppm) |
|---|---|---|---|
| 22-1-A | 12.9 | | 110 (20 minutes) |
| 22-1-B | 11.2 | | <10 (60 minutes) |
| 22-1-C | 11.9 | | 13 (100 minutes) |
| 22-1-D | 12.4 | | 15 (140 minutes) |
| 20-1-A | 13.8 | 360 (20 minutes) | |
| 20-1-B | 13.2 | 28 (60 minutes) | |
| 20-1-C | 13.5 | <10 (100 minutes) | |
| 21-4-A | 14.7 | | 47 (20 minutes) |
| 21-4-B | 14.6 | | 19 (60 minutes) |

Films dried at 60° C. for 6 h from chloroform and dioxane had high drug content (almost 100% recovery) and about 8% and 2% residual solvent, respectively. After extraction for different times, the residual solvent levels dropped to 360 ppm in 20 minutes to below detection limits in 100 minutes with about 92% drug recovery for chloroform films; and to 47 ppm in 20 minutes to 19 ppm in 60 minutes with about 100% drug recovery for dioxane films. It should be noted that the film thicknesses were different.

Films dried under ramping conditions from dioxane had only 0.2% residual solvent and 90% drug recovery. After extraction, the residual solvent levels dropped to 110 ppm in 20 minutes to about 10 ppm in 140 minutes with about 88% drug recovery. Drug recovery is lower due to exposure to high temperature (90° C.) for about 2 h during film drying.

Drying conditions of 60° C. for 6 h results in high drug recovery. Supercritical extraction time of 60 minutes seems to be sufficient to remove solvents to acceptable limits for all films.

Example IV

This example is for drug loaded PLGA films as summarized in the previous example. The films numbered 27-1, 27-4 and 27-6 were prepared from PLGA 85/15 with 20% barium sulfate and 15% sirolimus using stabilized dioxane. Films were dried at 50° C. for 1 h followed by 70° C. for 6 h. Films 27-1 and 27-6 were dried using double-sided configuration; and film 27-4 was dried using single sided configuration. Residual solvent and drug content in these films was about 4-5% and 12.5%, respectively.

Films were then extracted in a 500 ml vessel with I.D. of about 2.5". The extraction temperature was 35° C. and $CO_2$ pressure used was 77 Bar. Extraction time along with sample weight before and after extraction are given in the following tables:

TABLE 9

| Sample number | Wo (g) (Before extraction) | Wf (g) (After extraction) | % Change | $CO_2$ Flow rate (g/min) | Extraction Time (min) |
|---|---|---|---|---|---|
| 20-2 | 4.1467 | Xx | — | 30 | 60 |
| 20-3 | 4.1218 | 3.9644 | 3.8 | 30 | 100 |
| 21-3 | 2.2505 | 2.1597 | 4.0 | 30 | 110 |
| 21-1 | 2.3068 | 2.2158 | 3.9 | 30 | 60 |
| 27-1 | 3.1245 | 3.0193 | 3.4 | 30 | 100 |
| 27-6 | 3.5904 | Xx | — | 30 | 60 |

TABLE 10

| Sample I.D. | Residual Solvents (μg/g) | (%) | Sirolimus (%) Found | Corrected | Recovery |
|---|---|---|---|---|---|
| 20-2 | 186 (C) | 0.02 | 14.1 | 14.1 | 94.0 |
| 20-3 | 232 (C) | 0.02 | 14.0 | 14.0 | 93.6 |
| 21-1 | 537 (D) | 0.05 | 15.5 | 15.5 | 103.3 |
| 21-3 | 305 (D) | 0.03 | 13.1 | 13.1 | 87.1 |
| 27-1 | 10 (D) | 0.00 | 13.4 | 13.4 | 89.4 |
| 27-6 | 16 (D) | 0.00 | 12.3 | 12.3 | 81.8 |

Corrected (%) = Found/[(100 − % Residual Solvents)/100];
% Residual Solvents = ug/g Residual Solvents/10000
Recovery (%) calculated based on 15.0% sirolimus (theoretical value)
(C): Chloroform, (D): Dioxane Since some of the films from the above experiments showed high residual contents, three more films were extracted in the same system under the same temperature and pressure with higher $CO_2$ flow rate—80 g/min and 120 g/min respectively. The results are listed as follows:

TABLE 11

| Sample number | Wo (g) (Before extraction) | Wf (g) (After extraction) | % Change | $CO_2$ Flow rate (g/min) | Extraction Time (min) |
|---|---|---|---|---|---|
| 27-4 | 3.2936 | 3.1640 | 3.9 | 80 | 100 |
| 20-4 | 3.9425 | 3.6632 | 7.1 | 80 | 100 |
| 20-5 | 4.1715 | — | — | 120 | 60 |

TABLE 12

| Sample ID | Residual Solvents ug/g (ppm) | Type | Sirolimus (%) Found in Film | Corrected | Recovery * |
|---|---|---|---|---|---|
| 20-4 | 213 | Chloroform | 12.80 | 12.81 | 85.4 |
| 20-5 | 368 | Chloroform | 14.12 | 14.13 | 94.2 |
| 27-4 | 44 | Dioxane | 11.18 | 11.18 | 74.5 |

* Recovery calculated based on theoretical % of Sirolimus (15%)

* Recovery calculated based on theoretical % of Sirolimus (15%)

Example V

Several different films were prepared from PLGA 95/5 and 85/15 with polymer blends, 20% barium sulfate and 15% sirolimus using different solvents. The films used in this experiment are sunmmarized in the table below.

TABLE 13

| Sample ID | Film Description |
|---|---|
| 32-1 | PLA-PGA (85:15) with barium sulfate and sirolimus in BHT stabilized Dioxane |
| 32-2 | PLA-PGA (95:5) with barium sulfate and sirolimus in BHT stabilized Dioxane |
| 32-3 | PLA-PGA (85:15) with barium sulfate in BHT Stabilized Dioxane/ethyl acetate (25:75) |
| 32-4 | PLA-PGA (85:15) with barium sulfate and sirolimus in BHT stabilized Dioxane |
| 32-5 | PLA-PGA (95:5) with barium sulfate and sirolimus in BHT stabilized Dioxane |
| 32-6 | PLA-PGA (85:15) with barium sulfate in BHT Stabilized dioxane/ethyl acetate (25:75) |
| 34-1 | PLA-PGA (85:15)/5% PGA-PCL with barium sulfate and sirolimus in BHT stabilized dioxane |

TABLE 13-continued

| Sample ID | Film Description |
|---|---|
| 34-2 | PLA-PGA (85:15)/10% PGA-PCL with barium sulfate and sirolimus in BHT stabilized dioxane |
| 34-3 | PLA-PGA (95:5)/5% PGA-PCL with barium sulfate and sirolimus in BHT stabilize dioxane |
| 34-4 | PLA-PGA (85:15)/5% PGA-PCL with barium sulfate and sirolimus in BHT stabilized dioxane |
| 34-5 | PLA-PGA (85:15)/10% PGA-PCL with barium sulfate and sirolimus in BHT stabilized dioxane |
| 34-6 | PLA-PGA (95:5)/5% PGA-PCL with barium sulfate and sirolimus in BHT stabilized dioxane |
| 36-1 | PLA-PGA (95:5)/10% PGA-PCL with barium sulfate and sirolimus in BHT stabilized dioxane |
| 36-3 | PLA-PGA (85:15) with barium sulfate and sirolimus in BHT stabilized dioxane/acetone (25:75) |
| 36-4 | 6% PLA-PGA (95:5)/10% PGA-PCL with barium sulfate and sirolimus in BHT stabilized dioxane |
| 36-6 | 6% PLA-PGA (85:15) with barium sulfate and sirolimus in BHT stabilized dioxane/acetone (25:75) |

These films were extracted using the 500 ml vessel at 35° C. and 77 bar for 100 min with $CO_2$ flow=80 g/min. The residual solvent and sirolimus content for these films are summarized in the table below.

TABLE 14

| Sample I.D. | Sirolimus Contents (%) | Residual Solvents (ppm) | | |
|---|---|---|---|---|
| | | 1,4-Dioxane | Ethyl Acetate | Acetone |
| 32-1 | 14.5 | 148 | | |
| 32-2 | 13.9 | 117 | | |
| 32-3 | 15.0 | 17 | 2 | |
| 32-4 | 13.9 | 86 | | |
| 32-5 | 14.3 | 212 | | 8 |
| 32-6 | 14.0 | 252 | | 16 |
| 34-1 | 14.2 | 739 | | |
| 34-2 | 14.0 | 842 | | |
| 34-3 | 13.9 | 122 | | |
| 34-4 | 14.4 | 379 | | |
| 34-5 | 13.7 | 868 | | |
| 34-6 | 14.2 | 110 | | |
| 36-1 | 13.6 | 79 | | |
| 36-3 | 12.9 | 67 | | 4 |
| 36-4 | 14.1 | 82 | | |
| 36-5 | 13.8 | 66 | | 3 |

The drug recovery was very high and the solvent content was very low in all the films.

These experiments can be further scaled up in larger vessels to further optimize the extraction conditions.

Similar extraction experiments can be conducted for tubes containing similar polymer compositions prepared from a process that will allow undesirable amount of solvent. This method of extraction can also be used for removing other low molecular weight substances (e.g., ethylene oxide; monomers) from other device configurations such as coatings, stents, etc.

While specific embodiments of the present invention are described and illustrated hereinabove, it is clear that a person ordinarily skilled in the art can readily modify such specific embodiments consistent with the descriptions provided herein. It should therefore be recognized that the present invention is not limited to the specific embodiments illustrated hereinabove, but rather extends in utility to any other modification, variation, application, and embodiment, and accordingly all such other modifications, variations, applications, and embodiments are to be regarded as being within the spirit and scope of the invention.

What is claimed is:

1. A method for fabricating an implantable medical device comprising:
    forming a drug-containing polymeric composition comprising a biocompatible polymeric matrix with one or more therapeutic agents and one or more radiopaque agents incorporated into the implantable medical device, wherein said polymeric matrix further comprises one or more organic solvents, the polymeric matrix comprising at least two polymers;
    oven drying the drug-containing polymeric composition for a first period of time at a processing temperature of not higher than 60° C. so as to reduce solvent content in the polymeric matrix to an amount ranging from about 0.5 wt. % to about 10 wt. % of the total weight of the polymeric matrix; and
    subsequently removing additional solvents from the drug-containing polymeric composition after oven drying the composition utilizing a supercritical carbon dioxide process to reduce solvent content in the polymeric matrix to an amount less than about 10,000 ppm of the polymeric matrix, wherein the first period of time is selected to reduce porosity in the drug-containing polymeric composition during the supercritical carbon dioxide process.

* * * * *